US 6,632,213 B1

(12) United States Patent
Lehman et al.

(10) Patent No.: US 6,632,213 B1
(45) Date of Patent: Oct. 14, 2003

(54) ABSORBENT ARTICLE WITH A ROLLED LEG CUFF

(75) Inventors: John Ray Lehman, Neenah, WI (US); Mark Arthur Olson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/435,265

(22) Filed: Nov. 5, 1999

Related U.S. Application Data

(63) Continuation-in-part of application No. 09/290,414, filed on Apr. 13, 1999.

(51) Int. Cl.$^7$ .............................................. A61F 13/15
(52) U.S. Cl. ................................. 604/385.25; 604/386
(58) Field of Search ....................... 604/385.01, 385.24, 604/385.25, 385.28, 385.3, 389, 391, 386

(56) References Cited

U.S. PATENT DOCUMENTS

| | | | |
|---|---|---|---|
| 3,860,003 A | 1/1975 | Buell | 128/287 |
| 3,901,236 A | 8/1975 | Assarsson et al. | 128/284 |
| 4,076,663 A | 2/1978 | Masuda et al. | 260/17.4 GC |
| 4,286,082 A | 8/1981 | Tsubakimoto et al. | 526/240 |
| 4,636,207 A | 1/1987 | Buell | 604/370 |
| 4,661,102 A | 4/1987 | Shikata et al. | 604/385 A |
| 4,704,115 A * | 11/1987 | Buell | 604/385 |
| 4,704,116 A | 11/1987 | Enloe | 604/385 A |
| 4,720,415 A | 1/1988 | Vander Wielen et al. | 428/152 |
| 4,808,176 A | 2/1989 | Kielpikowski | 604/385.2 |
| 4,808,178 A | 2/1989 | Aziz et al. | 604/385.2 |
| RE33,106 E | 11/1989 | Beckestrom | 604/385.2 |
| 4,900,317 A | 2/1990 | Buell | 604/370 |
| 4,909,803 A | 3/1990 | Aziz et al. | 604/385.2 |
| 4,938,753 A | 7/1990 | Van Gompel et al. | 604/385.2 |
| 4,938,757 A | 7/1990 | Van Gompel et al. | 604/396 |
| 4,940,464 A | 7/1990 | Van Gompel et al. | 604/396 |
| 4,964,860 A | 10/1990 | Gipson et al. | 604/391 |
| 5,021,051 A | 6/1991 | Hiuke | 604/385.2 |

(List continued on next page.)

FOREIGN PATENT DOCUMENTS

| | | | | |
|---|---|---|---|---|
| WO | 96/14815 | 5/1996 | | A61F/13/15 |
| WO | 97/12571 | 4/1997 | | A61F/13/15 |
| WO | 98/14156 | 4/1998 | | A61F/13/15 |
| WO | 98/29080 | 7/1998 | | A61F/13/15 |

Primary Examiner—Weilun Lo
Assistant Examiner—Jamisue A. Webb
(74) Attorney, Agent, or Firm—Pauley Petersen & Erickson

(57) ABSTRACT

An absorbent garment having a pant-like configuration is constructed with strategically placed leg elastic, resulting in an aesthetically pleasing, finished look at the leg openings. Such strategic placements include securing the leg elastic to an outer cover and folding the outer cover over the elastic; or placing the elastic between a liquid-permneable body side liner and the outer cover and folding the outer cover over the elastic and securing the outer cover to the body side liner; or folding the outer cover more than once around the elastic. In any case, the distance between the leg elastic is nearly equal to the width dimension of the outer cover of the finished product. In addition to being aesthetically pleasing, the finished product eliminates the chance of exposing the leg elastic to the user. In an alternate embodiment, portions of the outer cover can extend laterally beyond an absorbent layer, thereby serving as seamless leak guards.

28 Claims, 5 Drawing Sheets

U.S. PATENT DOCUMENTS

| | | | |
|---|---|---|---|
| 5,085,654 A | 2/1992 | Buell | 604/370 |
| 5,087,255 A | 2/1992 | Sims | 604/385.1 |
| 5,110,403 A | 5/1992 | Ehlert | 156/580.1 |
| 5,234,422 A | 8/1993 | Sneller et al. | 604/385.2 |
| 5,246,433 A | 9/1993 | Hasse et al. | 604/396 |
| 5,286,543 A | 2/1994 | Ungpiyakul et al. | 428/74 |
| 5,308,346 A | 5/1994 | Sneller et al. | 604/385.2 |
| 5,358,500 A | 10/1994 | Lavon et al. | 604/385.2 |
| 5,368,584 A | 11/1994 | Clear et al. | 604/385.2 |
| 5,383,871 A | 1/1995 | Carlin et al. | 604/385.2 |
| 5,383,872 A | 1/1995 | Roessler et al. | 604/391 |
| 5,389,095 A | 2/1995 | Suzuki et al. | 604/385.2 |
| 5,389,168 A | 2/1995 | Litchholt et al. | 156/77 |
| 5,389,173 A | 2/1995 | Merkatoris et al. | 156/164 |
| 5,399,176 A | 3/1995 | Chen | 604/385.1 |
| 5,399,177 A | 3/1995 | Blaney et al. | 604/389 |
| 5,407,438 A | 4/1995 | Hedlund et al. | 604/385.2 |
| 5,411,498 A | 5/1995 | Fahrenkrug et al. | 604/385.2 |
| 5,413,654 A | 5/1995 | Igaue et al. | 156/161 |
| 5,425,726 A | 6/1995 | Shimizu et al. | 604/385.1 |
| 5,445,628 A | 8/1995 | Gipson et al. | 604/392 |
| 5,462,539 A | 10/1995 | Herman et al. | 604/385.1 |
| 5,464,401 A | 11/1995 | Hasse et al. | 604/385.1 |
| 5,489,282 A | 2/1996 | Zehner et al. | 604/385.1 |
| 5,496,298 A | 3/1996 | Kuepper et al. | 604/389 |
| 5,496,429 A | 3/1996 | Hasse et al. | 156/73.3 |
| 5,499,978 A | 3/1996 | Buell et al. | 604/385.2 |
| 5,503,919 A | 4/1996 | Litchholt et al. | 428/286 |
| 5,520,673 A | 5/1996 | Yarbrough et al. | 604/378 |
| 5,522,809 A | 6/1996 | Larsonneur | 604/361 |
| 5,527,300 A | 6/1996 | Sauer | 604/378 |
| 5,527,304 A | 6/1996 | Buell et al. | 604/385.2 |
| 5,531,729 A | 7/1996 | Coles et al. | 604/384 |
| 5,542,942 A | 8/1996 | Kline et al. | 604/385.2 |
| 5,542,943 A | 8/1996 | Sageser | 604/385.2 |
| 5,545,158 A | 8/1996 | Jessup | 604/385.2 |
| 5,554,145 A | 9/1996 | Roe et al. | 604/385.2 |
| 5,556,394 A | 9/1996 | Roe et al. | 604/385.2 |
| 5,558,660 A | 9/1996 | Dreier | 604/385.2 |
| 5,558,661 A | 9/1996 | Roe et al. | 604/385.2 |
| 5,569,234 A | 10/1996 | Buell et al. | 604/396 |
| 5,571,096 A | 11/1996 | Dobrin et al. | 604/383 |
| 5,577,540 A * | 11/1996 | Sageser | 156/211 |
| 5,591,150 A | 1/1997 | Olsen et al. | 604/385.1 |
| 5,591,151 A | 1/1997 | Hasse et al. | 604/385.1 |
| 5,591,152 A | 1/1997 | Buell et al. | 604/385.2 |
| 5,593,399 A | 1/1997 | Tanzer et al. | 604/368 |
| 5,593,401 A | 1/1997 | Sosalla et al. | 604/385.2 |
| 5,601,543 A | 2/1997 | Dreier et al. | 604/385.1 |
| 5,609,587 A | 3/1997 | Roe | 604/360 |
| 5,618,280 A | 4/1997 | Glackin et al. | 604/385.1 |
| 5,620,431 A | 4/1997 | LeMahieu et al. | 604/385.2 |
| 5,622,581 A | 4/1997 | Ducker et al. | 156/163 |
| 5,624,426 A | 4/1997 | Roe et al. | 601/385.2 |
| 5,634,916 A | 6/1997 | Lavon et al. | 604/385.1 |
| 5,643,244 A | 7/1997 | Yamaki et al. | 604/385.2 |
| H1674 H * | 8/1997 | Ames et al. | 604/389 |
| 5,716,478 A | 2/1998 | Boothe et al. | 156/302 |
| 5,735,838 A | 4/1998 | Rönnberg et al. | 604/385.2 |
| 5,858,012 A * | 1/1999 | Yamaki et al. | 604/358 |
| 6,306,122 B1 * | 10/2001 | Narawa et al. | 604/385.01 |

\* cited by examiner

ABSORBENT ARTICLE WITH A ROLLED LEG CUFF

This application is a continuation-in-part of U.S. patent application Ser. No. 09/290,414 filed Apr. 13, 1999, the disclosure of which is incorporated herein by reference.

FIELD OF THE INVENTION

This invention is directed to an absorbent garment, such as a training pant, swimsuit, diaper, incontinence garment or similar absorbent vehicle, wherein the leg elastic is strategically placed such that the distance between the leg elastic is roughly equal to the width dimension of the outer cover of the finished product. The strategic placement of the leg elastic provides for an aesthetically pleasing, finished look at the leg openings. Furthermore, the folding of the outer cover layer entraps the leg elastic material, thereby eliminating the chance of exposing the leg elastic to the user.

BACKGROUND OF THE INVENTION

Disposable absorbent garments having a pant-like configuration are used for child training pants, adult incontinence garments, diapers, swimsuits and the like. Referring to FIG. 1, a prior art pant-like absorbent garment 2 includes a waste containment section 4 and two side portions 6 and 8 defining a waist opening 10 and a pair of leg openings 12 and 14. The side panel 6 includes stretchable panels 18 and 20 joined together at seam 30. The side panel 8 includes stretchable panels 24 and 26 joined together at seam 33. Seams 30 and 33 extend longitudinally from the waist opening 10 to the leg openings 12 and 14 of the garment 2.

The waste containment section 4 includes multiple layers (not shown) including, for instance, a liquid-permeable inner layer, an absorbent core layer, and a liquid-impermeable outer cover layer 16 which faces away from the wearer. The waste containment section 4 also includes elasticized waist portions 22 on the front and back of the garment. The leg opening portions 12 and 14 also include elastic portions 46 which extend substantially around the portion of the leg openings defined by the waste containment section 4.

The elastic portions 46 are typically manufactured by situating elastic a set dimension from the edge of the outer cover 16. The excess material between the elastic and the edge of the outer cover 16 results in a ruffled, unfinished appearance at the leg openings 12 and 14. Current pant designs have the elastic sandwiched between a cloth layer and a polymer layer of the outer cover 16, while current diaper designs have the elastic attached to an inside surface of the polymer layer of the outer cover 16. Both methods result in a ruffled, unfinished appearance at the leg openings 12 and 14. Furthermore, when the elastic is attached to an inside surface of the garment, the elastic is exposed to the user's skin, which neither looks good nor feels good. With the growing trend of disposable pants being worn without a coverup, such as, for example, disposable swimsuits, a neater, more finished appearance is a desirable trait for such garments.

The disposable garment also includes leak guards in both leg openings, which help prevent lateral leakage of waste material through the leg openings. The leak guards have commonly been provided by elasticized flap portions 50 which are connected to the interior of the garment along the lower part of each leg opening. During use, the elasticized flap portions 50 fit snugly against the wearer and effectively block most spillage of waste material from the leg openings.

When flap portions 50 are used for the leak guards, a separate manufacturing step is required to attach the flap material to the garment. Generally, the flaps 50 have been joined via seams 52. During active use, some separation at the seams 52 can occur, resulting in failure of the flaps 50 to serve as effective leak guards. Providing a seam which is both leakproof and durable has been challenging, and has added to manufacturing costs. To solve this problem, seamless leak guards were disclosed in the parent U.S. application Ser. No. 09/290,414, referenced above. However, the parent application does not thoroughly address the ruffling caused by elastic portions 46.

SUMMARY OF THE INVENTION

The present invention is directed to a disposable pant-like absorbent garment with or without seamless leak guards, in which the leg elastic is strategically placed at a location on the outer cover layer to prevent a ruffled, unfinished appearance at the leg openings. In the resulting garment, the distance between the leg elastic is nearly equal to the width dimension of the outer cover of the finished product. In one embodiment, the elastic may be secured to the outer cover layer near its edge, and the outer cover layer folded over the elastic and sealed to itself. In another embodiment, the elastic may be placed between a liquid-permeable body side liner and the outer cover layer near its edge, with the outer cover layer folded over both the elastic and part of the body side liner, and secured to the body side liner. In another embodiment, the outer cover layer may be folded more than once around the elastic. In addition to being aesthetically pleasing, the finished product eliminates the chance of exposing the leg elastic to the user.

As described in the parent application, instead of using flaps, seamless leak guards may be provided by extending the liquid-impermeable outer cover layer substantially beyond the absorbent layer on both sides, and to a higher location on the garment and on the wearer. The outer cover extensions on both sides can be reinforced at their edges by the elastic leg bands which pull the outer cover extensions upward and away from the absorbent layer, and against the wearer's body. The lateral extensions of the outer cover material, combined with the upward pulling of the elastic leg bands, may provide the garment with seamless leak guards not requiring separately attached flaps. However, the present invention is not limited to the use of seamless leak guards, but is also applicable to garments having the conventional side flaps.

With the foregoing in mind, it is a feature and advantage of the invention to provide a disposable pant-like absorbent garment with strategically placed leg elastic to produce an aesthetically pleasing, finished appearance around the leg openings.

It is also a feature and advantage of the invention to provide a disposable pant-like absorbent garment wherein the user's legs are not exposed to the leg elastic.

It is a further feature and advantage of the invention to provide a disposable absorbent garment with a non-ruffled, finished appearance around the leg openings either with seamless leak guards, or with attached flaps.

DETAILED DESCRIPTION OF THE PRESENTLY PREFERRED EMBODIMENTS

Figure 1:
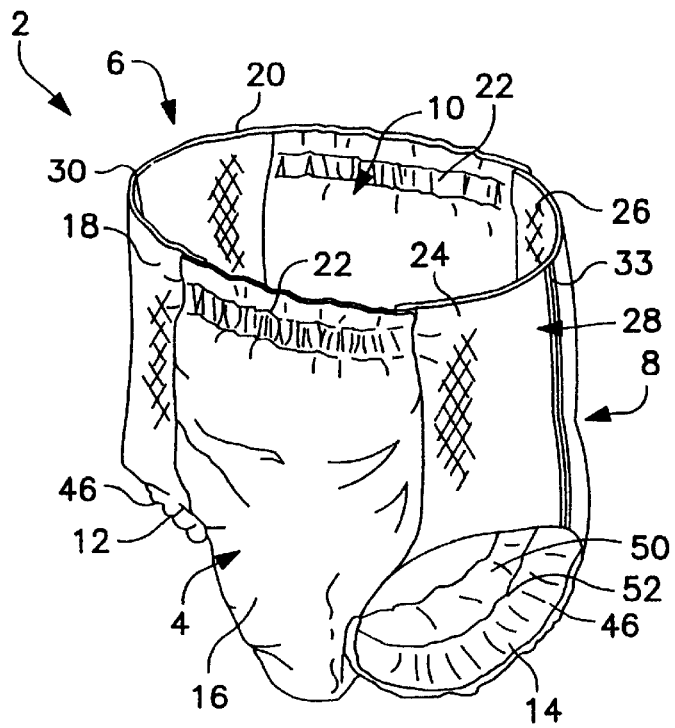
FIG. 1 (described above) is a perspective view of a prior art disposable absorbent garment with a ruffled appearance around the leg openings, in which the leak guards are provided by attached flaps.

While the invention is applicable to garments having seamless leak guards or conventional flap leak guards, the preferred embodiments are described with respect to a garment having seamless leak guards. Referring to FIGS. 2–9 of the drawings, an absorbent garment 2 of the invention has a pant-like configuration useful for diapers, child training pants, child swimwear, adult incontinence articles, and the like. The garment 2 includes a waste containment section 4 having a front portion 5 and a rear portion 7 joined by a central portion 15, and two side portions 6 and 8, each of which is connected at its edges to the front and rear portions. The side panel 6 includes stretchable panels 18 and 20 joined to each other along seam 30, and joined to the waste containment section along seams 29 and 31. Each of the seams 29, 30 and 31 is longitudinally oriented, and extends from the top of the waist opening 10 to the leg opening 12. The side panel 8 includes stretchable panels 24 and 26 joined to each other along seam 33, and joined to the waste containment section along seams 32 and 34. Each of the seams 32, 33 and 34 is longitudinally oriented, and extends from the top of the waist opening to the leg opening 14.

The longitudinal seams 29–34 may be formed by conventional methods including, without limitation, ultrasonic welding, thermal bonding, adhesive bonding, stitch bonding and the like. Ultrasonic welding is a presently preferred technique. The various bonding techniques are conventional, and are neither critical nor limiting as to the present invention.

Figure 2:
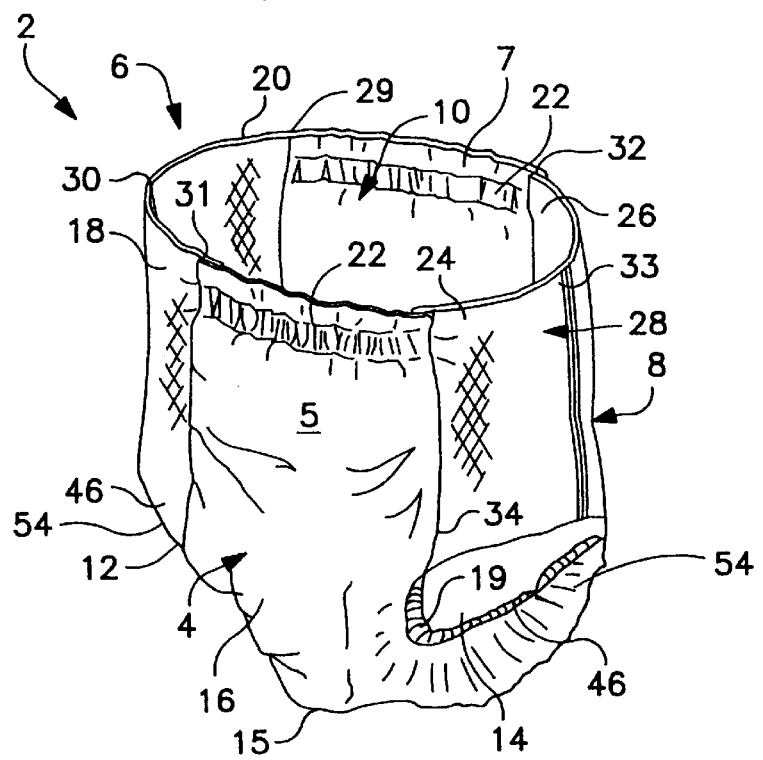
FIG. 2 is a perspective view of one embodiment of a flapless disposable absorbent garment of the invention with a rolled edge leg cuff. As explained above, the rolled leg cuff may also be provided on garments using conventional flaps for leak guards.

The stretchable side panels 6 and 8 can be constructed of conventional woven or nonwoven materials, formed from a wide variety of elastic and stretchable polymers. The terms "elastic" and "stretchable" include any material which can be stretched, and which tends to return to its original shape when relaxed. Suitable polymers include without limitation block copolymers of polystyrene, polyisoprene and polybutadiene; copolymers of ethylene, natural rubbers and urethanes; and combinations of the foregoing. Particularly suitable are styrene-butadiene block copolymers sold by Shell Chemical Co. under the trade name KRATON®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels. As shown in FIG. 2, the stretchable side panels are preferably rectangular in shape, and preferably extend from the top of the waist opening 10 to the leg openings 12 and 14. The side panels may also be laminates of multiple layers, and are preferably breathable to water vapor but impervious to liquids.

The waste containment section 4 includes a substantially liquid-impermeable outer cover layer 16, an absorbent layer 17, a liquid-permeable surge layer 13, and a liquid-permeable body side liner 21. These layers are constructed of conventional materials, and are bound together using conventional adhesives, as described below. In accordance with the invention, when seamless leak guards are incorporated in the garment 2, the outer cover layer 16 is much wider than the absorbent layer 17, especially in the central portion 15 of the absorbent garment between the leg openings 12 and 14. Alternatively, the outer cover layer 16 can be roughly equal in width with the absorbent layer 17.

In an embodiment wherein the portions 54 of the outer cover 16 extend beyond the absorbent layer 17, the extended portions 54 serve as seamless leak guards. By "seamless," it is meant that the leak guards are not separately attached and, thus, do not require a seam for attachment to the waste containment section 4. To effectively serve as leak guards, the difference in width between the absorbent layer and outer cover (between folded edges 55 and 57 in FIG. 3) must be substantial, as opposed to trivial, in the central region 15 between the leg openings. Generally, the outer cover 16 is at least about 40% wider than the absorbent layer 17 in the central region 15. Preferably, the outer cover 16 is at least about 60% wider than the absorbent layer 17 in the central region 15. More preferably, outer cover 16 is at least about 80% wider, and most preferably at least about 100% wider than absorbent layer 17 in central region 15 on the underside of the garment.

Figure 3:
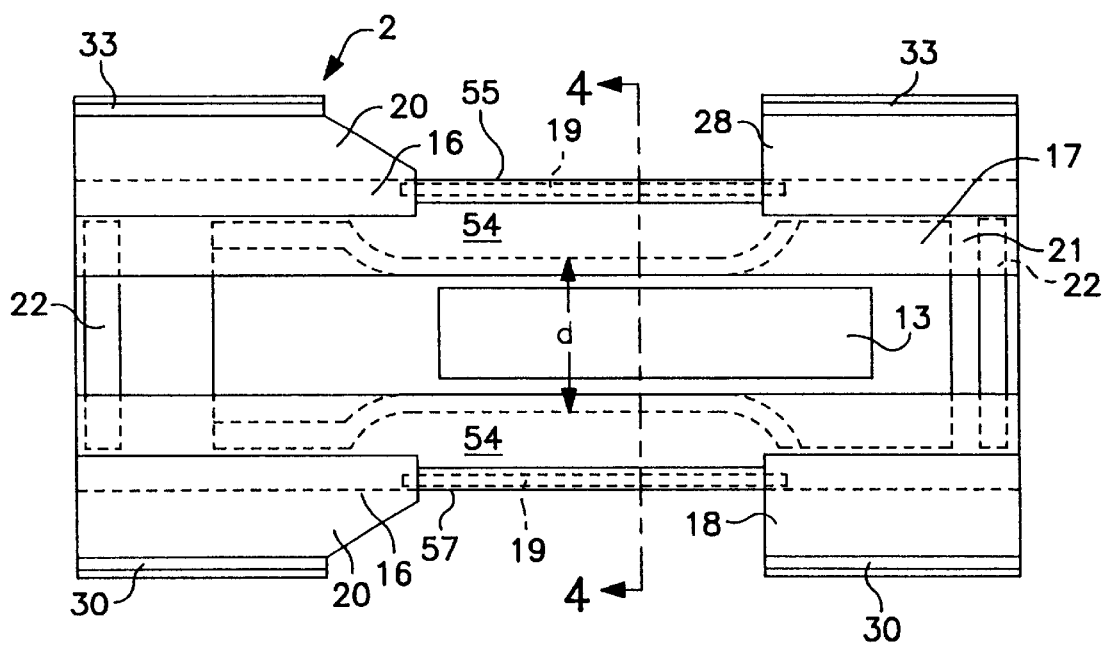
FIG. 3 is a plan view of a garment of the invention with strategically placed leg elastic, disconnected at the side seams, and laid out flat.

The seamless leak guards may also be defined with reference to FIGS. 2–3, in terms of the shortest distance "d" between the first and second leg openings measured along a line which follows the outer contour of central region 15 of waste containment section 4. The leak guards should constitute at least about 25% of this distance, preferably at least about 35% of this distance, more preferably at least about 45%, most preferably at least about 50%.

In the embodiment shown in FIG. 3, the outer cover 16 is about 100% wider than the absorbent layer 17 in the central region. Furthermore, the outer cover 16 is configured as a perfect rectangle from the front to the back of the garment, and through the central region. The rectangular configuration of outer cover 16 facilitates ease of manufacture of the outer cover, ease of attachment of adhesives and elastic straps to the outer cover, and provides for large and effective leak guards on both sides of the absorbent layer in the central region.

Elastic bands 19 are mounted to the outer cover layer 16 as shown, for instance, in FIG. 3. The elastic bands 19 preferably extend through the central region 15, and substantially parallel to fold edges 55 and 57 of the outer cover 16, defining the leg openings. The elastic bands 19 may be attached to the outer cover 16 by a variety of techniques including adhesive bonding, ultrasonic bonding, thermal bonding, stitch bonding or other conventional techniques. Suitable adhesives include spray adhesives, hot melt adhesives, self-adhering elastomeric materials and the like. Furthermore, an elastic adhesive can be sprayed onto the elastic bands 19 and the outer cover 16 prior to folding the outer cover 16, or the elastic adhesive can be intermittently applied to the elastic bands 19 prior to folding the outer cover 16, thereby causing the elastic bands 19 to function as drawstrings within the folded outer cover. An adhesive layer (not shown) may be positioned between the elastic bands 19 and either layer (35 or 37), preferably the outer layer 35, of the outer cover 16. Often, the elastic bands will be applied in the stretched condition to the outer cover 16, and then allowed to retract, causing gathering of the outer cover at the folded edges 55 and 57 when the bands 19 are retracted. There are preferably at least two elastic bands 19, more preferably at least four elastic bands 19, adjacent the fold edges 55 and 57 of the outer cover 16.

Figure 4:
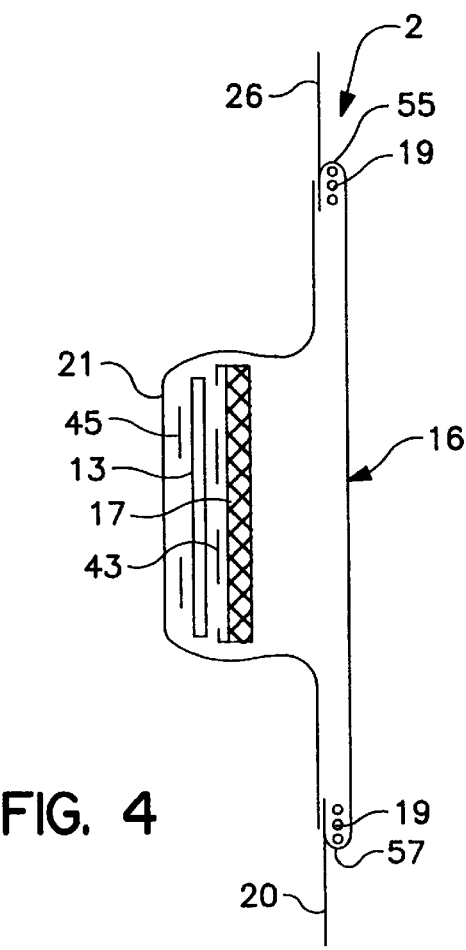
FIG. 4 is an expanded schematic sectional view of one embodiment of a garment of the invention taken along line 4—4 in FIG. 3 and showing each layer of the garment.

FIG. 4 shows one embodiment, wherein the elastic bands 19 are attached to the outer cover 16 slightly inward from, or in line with, the fold edges 55 and 57, with the outer cover being folded over to envelop and encapsulate the elastic bands 19. Again, the folding over of the edges may occur in either direction, namely toward or away from the body-facing side of the outer cover 16. Furthermore, as shown in the embodiment in FIG. 5, the elastic bands 19 can be placed between the liquid-permeable body side liner 21 and the outer cover 16 near its edge, with the outer cover 16 folded over both the elastic bands 19 and part of the body side liner 21, and secured to the body side liner 21. In yet another embodiment, shown in FIG. 6, the outer cover 16 may be folded or rolled over the elastic bands 19 more than once, thereby fully entrapping the elastic bands 19 and completely eliminating any exposure of the elastic to the user. In each of the embodiments, once the outer cover 16 is folded over the elastic bands 19, the width of the outer cover 16 is within about 2.5 cm of the shortest distance between the elastic bands 19, preferably within about 1.0 cm of the shortest distance between the elastic bands 19. More preferably, the width of the folded outer cover 16 is roughly equal to the distance between the outermost elastic bands 19.

Figure 7:
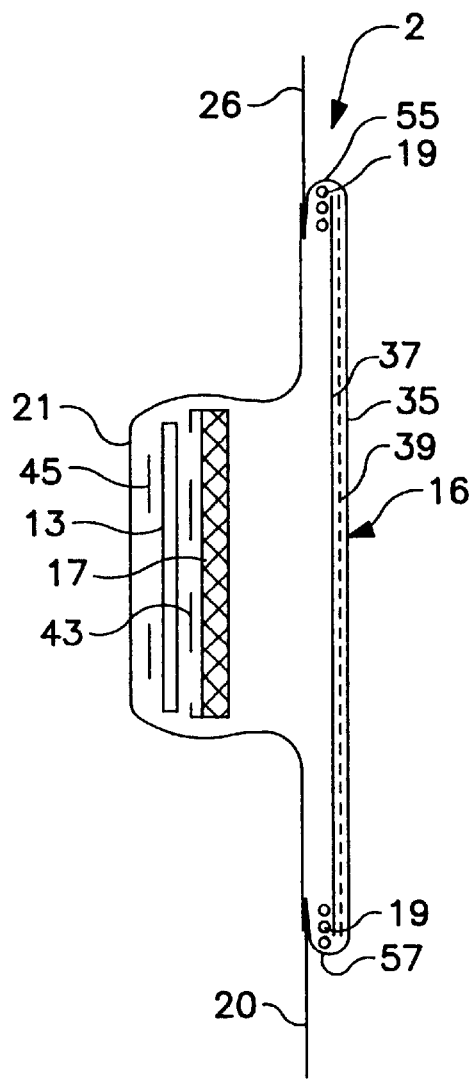
FIG. 7 is an expanded schematic sectional view of yet another embodiment of a garment of the invention showing each layer of the garment.

Referring to FIGS. 3 and 7–9, the outer cover 16 can include two layers 35 and 37 joined by adhesive 39, as explained below. FIG. 7 shows one embodiment wherein the elastic bands 19 are sandwiched between the inner layer 37 of the outer cover 16 and the folded over outer layer 35 of the outer cover 16. In a preferred embodiment shown in FIG. 8, the elastic bands 19 are sandwiched between the inner layer 37 of the outer cover 16 and the outer layer 35 of the outer cover 16, and the outer layer 35 is subsequently folded over the inner layer 37. In a further embodiment shown in FIG. 9, the inner layer 37 and the outer layer 35 remain adhered to one another without the elastic bands 19 between them. Instead, the elastic bands 19 are enveloped within a fold of the two-layered outer cover 16, such that the elastic bands 19 are in contact solely with the inner layer 37. As in the embodiments in FIGS. 4–6, in each of the embodiments in FIGS. 7–9, the elastic bands 19 are slightly inward from, or in line with, the fold edges 55 and 57.

The material used for the elastic bands 19 may be conventional, as described below. However, in order for the elastic bands 19 to optimize the performance of leak guards defined by outer cover extensions 54, it is important that the elastic bands pull the folded edges 55 and 57 mostly upward and toward the wearer. This upward pulling of the folded edges 55 and 57 of the leak guards, toward the wearer, is best accomplished when the outer cover layer 16 is substantially rectangular, as shown in FIG. 3. When the elastic bands 19 are placed slightly inward from the folded edges 55 and 57 of a rectangular outer cover, the bands 19 are oriented substantially in the direction of the desired pulling force (i.e., upward in both the front and back of the garment). If the elastic bands 19 were instead mounted to curve inward in the central crotch region then the vectoral component of the pulling force during wear, which pulls the folded edges 55 and 57 upward, would be less pronounced. Depending on the size of the wearer and the size of the garment 2, the elastic bands 19 will also, to a degree, pull the folded edges 55 and 57 inward against the wearer's skin.

The elastic bands 19 may be in the form of single or multiple bands per leg. A wide variety of elastic materials may be employed. Examples include a film or meltblown web formed using block or graft copolymers of butadiene, isoprene, styrene, ethylene-methyl acrylate, ethylene-vinyl acetate, ethylene-ethyl acrylate or blends thereof. One preferred elastomer is a block copolymer of styrene-ethylbutadiene-styrene. Specific materials of which elastic bands 19 can be made are the Kraton G series from Shell Chemical Company, such as Kraton G-1650, Kraton G-1652, Kraton GX-1657 and preferably Kraton G-2740X. Also, the Kraton D series can be used, as well as polyester elastomeric materials, polyurethane elastomeric materials and polyamide elastomeric materials. Elastomeric single-site or metallocene-catalyzed olefin polymers and copolymers can also be employed. Also, elastic bands 19 can be made of an activatable material applied in an unstretched condition, and activated by heat, light or moisture or radiation to cause shrinkage and elasticity. Activatable elastic materials can be obtained from the 3M Company.

Each leg elastic band 19 preferably has a width of about 0.05 inch to about 3 inches, more preferably about 0.15 inch to about 1.5 inches, most preferably about 0.25 inch to about 1.0 inch. Each elastic band 19 preferably has elongation of 25–350%, more preferably about 30–260%, most preferably about 35–200%. The length of elastic bands 19 should substantially cover the lengths of the leak guards 54, so that both fastened ends of the elastic bands 19 are oriented substantially upward (toward the waist area) on the wearer. If the elastic bands are not long enough that both ends point toward the wearer's waist, then the upward pulling force exerted by the bands on folded edges 55 and 57 of leak guards 54 will be reduced. Depending on the garment size, the elastic bands 19 may have a length of at least about 2 inches, preferably at least about 3 inches, more preferably at least about 4 inches.

Once the outer cover 16 is folded, the distance between the elastic bands 19 is within about 2.5 cm of, preferably within about 1.0 cm of, the distance between the folded edges 55 and 57 of the outer cover 16, which is the width of the folded outer cover 16. Most desirably, the distance between the outermost elastic bands 19 is about equal to the width of the folded outer cover 16. The close proximity of the elastic bands 19 to the folded edges 55 and 57 prevents excess gathered material from overhanging into the leg openings 12 and 14, thereby eliminating a ruffled look and creating an aesthetically pleasing, finished look.

Figure 8:
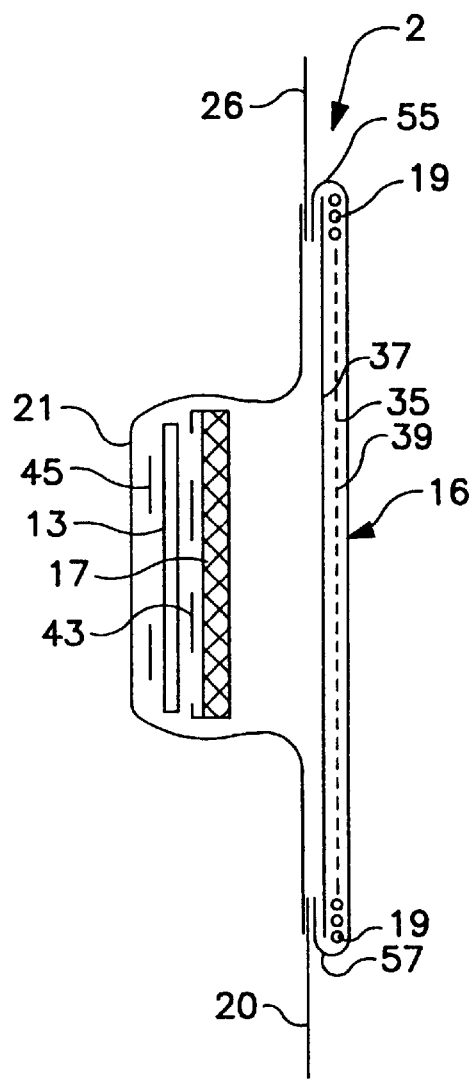
FIG. 8 is an expanded schematic sectional view of still another embodiment of a garment of the invention showing each layer of the garment.
Figure 9:
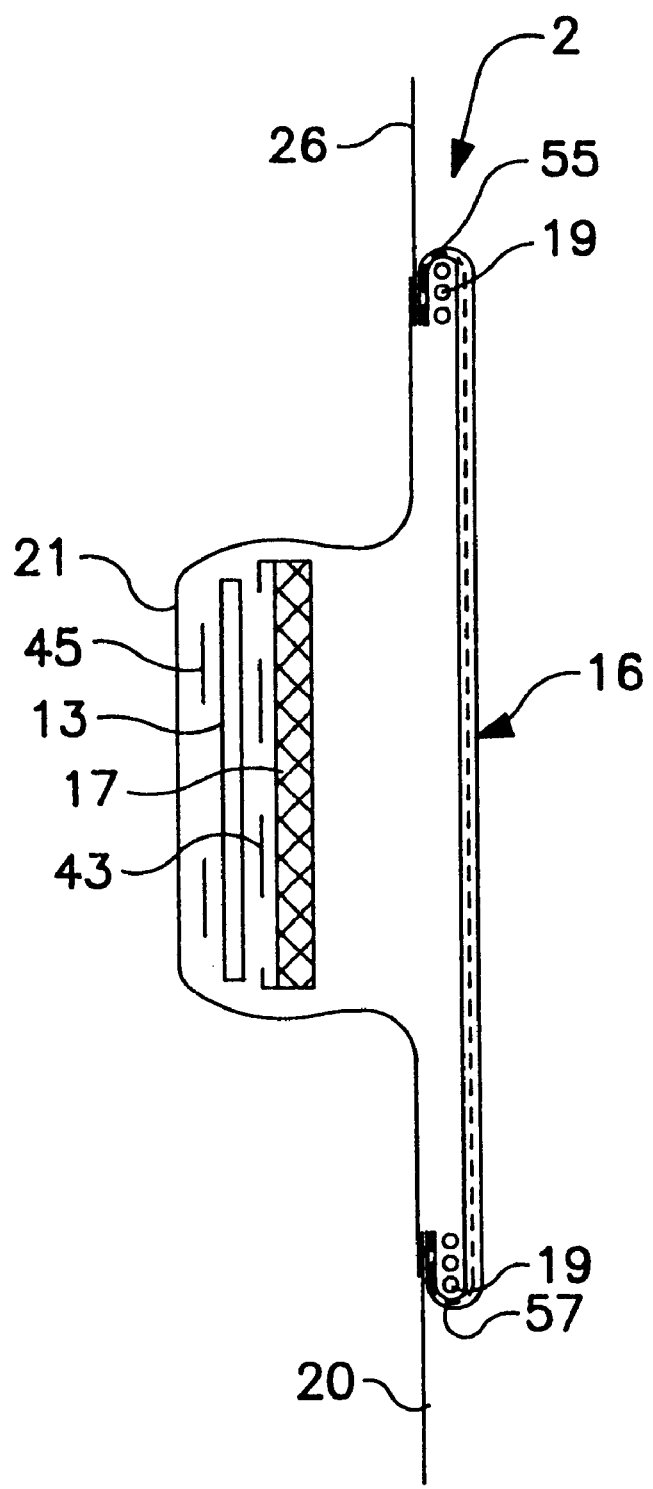
FIG. 9 is an expanded schematic sectional view of a further embodiment of a garment of the invention showing each layer of the garment.

The outer cover 16 may include a single layer, or may include multiple layers joined together. The outer cover 16, as shown in FIGS. 7–9, includes two layers 35 and 37, joined by an outer cover adhesive layer 39. The outer cover 16 can be made from a wide variety of woven or nonwoven material, films, or a film-coated nonwoven material, including, for instance, cast or blown films of polyethylene, polypropylene, polyester or blends thereof The outer cover 16 may also be a composite of a bonded carded or spun-bonded or meltblown material, for example, a spunbonded-meltblown composite of thermoplastic material or a spunbonded-meltblown-spunbonded thermoplastic material, wherein the spunbonded layer can provide a cloth-like texture and the meltblown layer can provide liquid imper-meability. Materials of which the outer cover 16 can be made include nonwovens having a high basis weight, such as about 0.4 ounces per square yard, or greater.

The outer cover 16 can also include extruded films of polyolefin polymers or copolymers, or other thermoplastic materials. Generally the outer cover 16 will have a length from about 12 inches to about 30 inches, and a width from about 3 inches to about 20 inches, depending on the wearer's size. In the embodiment shown in FIG. 4, the outer cover 16 may include a woven or nonwoven cloth outer layer 35 and liquid-impervious film inner layer 37, joined by adhesive layer 39. Layers 35 and 37 may be joined using the same adhesives, or other bonding techniques, described above for the attachment of elastic bands 19.

Figure 5:
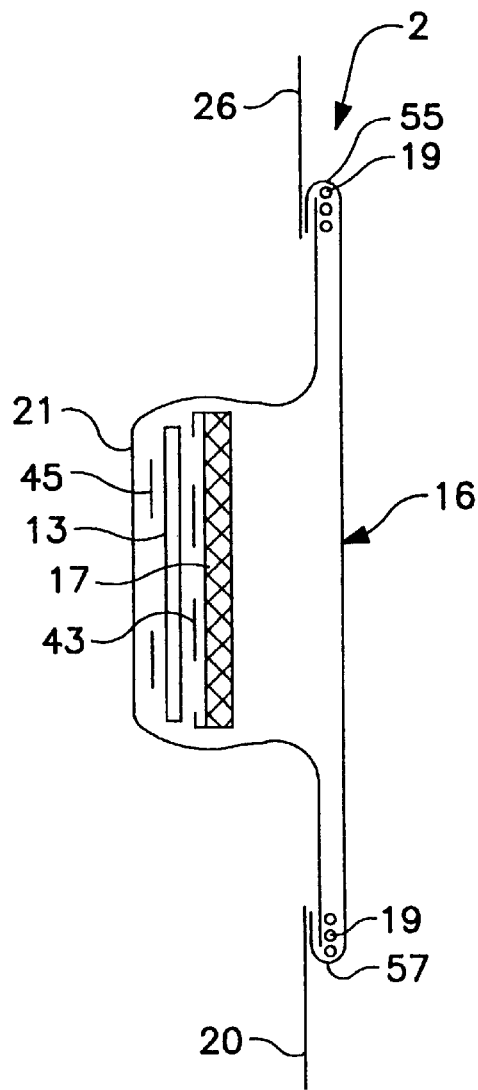
FIG. 5 is an expanded schematic sectional view of another embodiment of a garment of the invention showing each layer of the garment.
Figure 6:
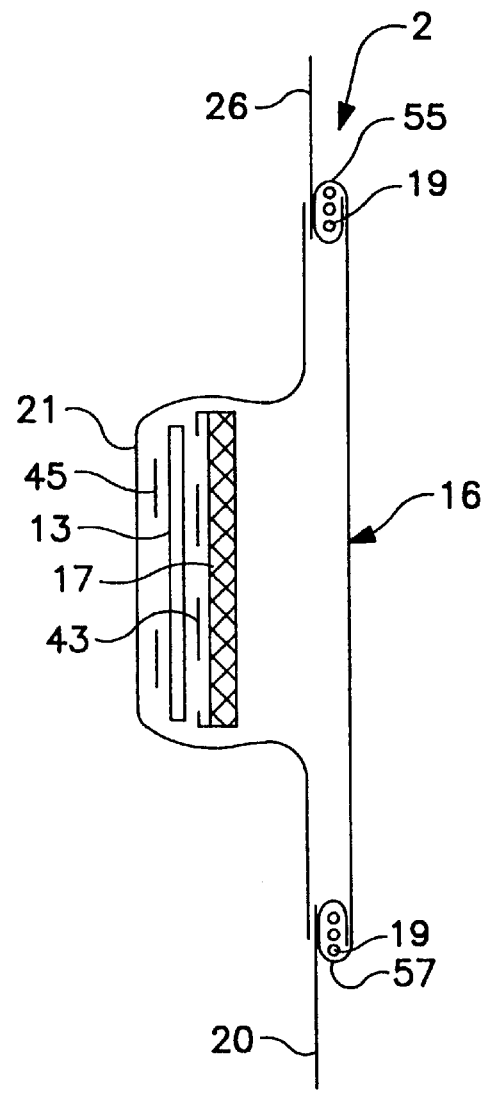
FIG. 6 is an expanded schematic sectional view of yet another embodiment of a garment of the invention showing each layer of the garment.

The outer cover 16, absorbent layer 17, surge layer 13 and body side liner 21 may also be joined together using ultrasonic bonding, thermal bonding, stitch bonding, or any of the adhesive materials described above. As shown in FIG. 5, the end regions of liner 21 may be tucked between the folded over regions of the outer cover 16 and bonded into place. This way, the surge layer and absorbent layer are surrounded by the liner 21 and outer cover 16. Surge layer 13 may be bonded to absorbent layer 17 using adhesive layer 43, and to body side liner 21 using adhesive layer 45. As shown in FIG. 3, the absorbent layer 17, surge layer 13 and body side liner 21 are substantially narrower than the outer cover 16 in the central region 15 of the garment 2. The layers 17, 13 and 21 are also somewhat narrower than the outer cover 16 in the regions corresponding to the front and back of the garment.

In the vicinity of the waist opening 10, waist elastic regions 22 may be attached to or embedded within the garment. The waist elastic regions 22 may include single or multiple elastic bands constructed from the same materials as leg elastic bands 19. Waist elastic regions 22 in the front and back of the garment preferably have lengths which are nearly the same, or slightly shorter than the width of the outer cover 16. The waist elastic bands may be attached to the outer cover 16 using the same techniques described above for attaching leg elastic bands 19.

Absorbent layer 17 can be made of wood pulp fluff or a mixture of wood pulp fluff and a superabsorbent material, or a wood pulp fluff integrated with a thermoplastic absorbent material treated with a surfactant. Thermal binders, such as Pulpex® can be used in blends or layering with the fluff and superabsorbent. Absorbent layer 17 can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Vander Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Both the surge layer 13 and body side liner 21 are constructed from highly liquid pervious materials. These layers function to transfer liquid from the wearer to the absorbent layer 17. Suitable materials include porous woven materials, porous nonwoven materials, and apertured films. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. Either layer may also be an apertured plastic film. The various layers of the garment 2 have dimensions which vary depending on the size and shape of the wearer.

The resulting product is an absorbent garment having an aesthetically pleasing, finished look about the leg openings 12 and 14. The strategically placed elastic leg bands 19 are also hidden from the user's sight and touch. The product may or may not comprise seamless leak guards 54 that not only reduce manufacturing costs, but also provide better leakage protection than prior art flaps joined to the garment with seams. The absorbent garment can be sized and tailored for a wide variety of uses including, for example, diapers, training pants, swimwear, adult incontinence garments, and the like.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent garment, comprising:
a waste containment section having front and rear portions, and a central region;
first and second side panels, each comprising an elastic material and joined to the front and rear portions of the waste containment section;
the waste containment section and side panels defining a waist opening and first and second leg openings;
the waste containment section including at least a liquid-permeable body side liner, an absorbent layer and a substantially liquid-impermeable outer cover, the outer cover having at least two layers; and
elastic bands positioned between at least two layers of the outer cover and substantially aligned with outer edges of at least one layer of the outer cover in the central region, each of the elastic bands extending from one of the first and second side panels at the front portion and along the central region to the same side panel at the rear portion, wherein the outer edges of the at least one layer of the outer cover are folded more than once over the elastic bands, such that a difference of a distance between the elastic bands along the outer edges of the outer cover and a width of the outer cover after the outer cover has been folded over the elastic bands is within about 2.5 cm.

2. The absorbent garment of claim 1, wherein the difference of the distance between the elastic bands along the outer edges of the outer cover and the width of the outer cover after the outer cover has been folded over the elastic bands is within about 1.0 cm.

3. The absorbent garment of claim 1, wherein the distance between the elastic bands is about equal to the width of the outer cover after the outer cover has been folded over the elastic bands.

4. The absorbent garment of claim 1, wherein the outer cover is folded inwardly toward a wearer's body.

5. The absorbent garment of claim 1, wherein the outer cover is folded outwardly away from a wearer's body.

6. The absorbent garment of claim 1, wherein the outer cover layer has a substantially rectangular shape when laid out flat.

7. The absorbent article of claim 1, comprising an adult incontinence garment.

8. The absorbent garment of claim 1, wherein each side panel comprises a plurality of adjacent panels.

9. The absorbent garment of claim 1, comprising a diaper.

10. The absorbent garment of claim 1, comprising swimwear.

11. The absorbent garment of claim 1, comprising child training pants.

12. An absorbent garment, comprising:
a waste containment section having front and rear portions, and a central region;
first and second side panels, each joined to the front and rear portions of the waste containment section;
the waste containment section and side panels defining a waist opening and first and second leg openings;
the waste containment section including at least a liquid-permeable body side liner, an absorbent layer and a substantially liquid-impermeable outer cover, the outer cover having at least one layer; and
elastic bands substantially aligned with outer edges of the at least one layer of the outer cover in the central region, each of the elastic bands extending from one of the first and second side panels at the front portion and along the central region to the same side panel at the rear portion, wherein the elastic bands are between the body side liner and the outer cover, and the outer edges of the at least one layer of the outer cover are folded more than once over the elastic bands, the folded portion of the outer cover underlying the body side liner, with the folded portion of the outer cover secured to the body side liner.

13. The absorbent garment of claim 12, wherein the substantially liquid-impermeable outer cover has a substantially rectangular shape when laid out flat.

14. The absorbent garment of claim 12, wherein the body side liner has a first width in the central region, and the outer cover has a second width in the central region, wherein the second width is greater than the first width.

15. The absorbent garment of claim 14, wherein the second width is about equal to the first width.

16. The absorbent garment of claim 12, wherein the outer cover comprises a substantially liquid impervious polyolefin film.

17. The absorbent garment of claim 16, wherein the outer cover further comprises a nonwoven polyolefin web.

18. An absorbent garment, comprising:
a waste containment section having front and rear portions, and a central region, the central region including a liquid-permeable body side liner and an outer cover;
first and second side panels, each joined to the front and rear portions of the waste containment section;
the waste containment section and side panels defining a waist opening and first and second leg openings; and
at least one elastic band substantially aligned with a first outer edge of the outer cover between the front portion and the rear portion of the waste containment section and at least one elastic band substantially aligned with a second outer edge of the outer cover between the front portion and the rear portion of the waste containment section, wherein the first outer edge is folded more than once over the at least one elastic band substantially aligned with the first outer edge within the central region of the waste containment section and the second outer edge is folded more than once over the at least one elastic band substantially aligned with the second outer edge within the central region of the waste containment section, the folded portions along each of the first and second outer edges of the outer cover underlying the body side liner.

19. The absorbent garment of claim 18, wherein the waste containment section further comprises elastic bands near the waist opening.

20. The absorbent garment of claim 18, wherein the elastic bands are folded inwardly toward a wearer's body.

21. The absorbent garment of claim 18, wherein the elastic bands are folded outwardly away from a wearer's body.

22. The absorbent garment of claim 18, wherein the waste containment section comprises at least an absorbent layer and a substantially liquid-impermeable outer cover having seamless leak guards defined by portions of the outer cover extending laterally beyond the absorbent layer in the central region and partially surrounding both leg openings, wherein the seamless leak guards constitute at least about 25% of a distance defined by the shortest line which joins the two leg openings through an outer contour of the central region.

23. The absorbent garment of claim 22, wherein the seamless leak guards constitute at least about 35% of the distance defined by the shortest line which joins the two leg openings through the outer contour of the central region.

24. The absorbent garment of claim 22, wherein the seamless leak guards constitute at least about 45% of said distance.

25. The absorbent garment of claim 22, wherein the seamless leak guards constitute at least about 50% of said distance.

26. The absorbent garment of claim 22, wherein the waste containment section further comprises a surge layer between the body side liner and the absorbent layer.

27. The absorbent garment of claim 22, wherein the outer cover comprises a plurality of layers, at least one of which is substantially liquid-impermeable.

28. The absorbent article of claim 18, wherein the first and second side panels comprise an elastic material.

* * * * *